(12) United States Patent
Custelcean et al.

(10) Patent No.: US 10,583,387 B2
(45) Date of Patent: Mar. 10, 2020

(54) GUANIDINE COMPOUNDS FOR CARBON DIOXIDE CAPTURE

(71) Applicant: UT-Battelle, LLC, Oak Ridge, TN (US)

(72) Inventors: Radu Custelcean, Beavercreek, OH (US); Neil Justin Williams, Knoxville, TN (US); Charles Aaron Seipp, Beavercreek, OH (US)

(73) Assignee: UT-Battelle, LLC, Oak Ridge, TN (US)

( * ) Notice: Subject to any disclaimer, the term of this patent is extended or adjusted under 35 U.S.C. 154(b) by 17 days.

(21) Appl. No.: 15/978,323

(22) Filed: May 14, 2018

(65) Prior Publication Data

US 2018/0345207 A1     Dec. 6, 2018

Related U.S. Application Data

(60) Provisional application No. 62/514,997, filed on Jun. 5, 2017, provisional application No. 62/647,052, filed on Mar. 23, 2018.

(51) Int. Cl.
*B01D 53/62* (2006.01)
*B01D 53/14* (2006.01)
(Continued)

(52) U.S. Cl.
CPC ..... *B01D 53/1475* (2013.01); *B01D 53/1493* (2013.01); *C07C 279/12* (2013.01);
(Continued)

(58) Field of Classification Search
None
See application file for complete search history.

(56) References Cited

U.S. PATENT DOCUMENTS 4,120,789 A * 10/1978 Fusco ................... C02F 1/5272
                                                              210/729
8,246,731 B2    8/2012 Lackner et al.
(Continued)

OTHER PUBLICATIONS

International Search Report and Written Opinion dated Sep. 18, 2018 issued in PCT/US18/32502.
(Continued)

*Primary Examiner* — Daniel Berns
(74) *Attorney, Agent, or Firm* — Scully, Scott, Murphy & Presser, P.C.

(57) ABSTRACT

A method for removing carbon dioxide from a gaseous source, the method comprising: (i) contacting said gaseous source with an aqueous solution of a carbon dioxide sorbent that reacts with carbon dioxide to form an aqueous-soluble carbonate or bicarbonate salt of said carbon dioxide sorbent; (ii) contacting the aqueous solution from step (i) with a bis-iminoguanidine carbon dioxide complexing compound, which is different from the carbon dioxide sorbent, to result in precipitation of a carbonate or bicarbonate salt of said carbon dioxide complexing compound and regeneration of the carbon dioxide sorbent; and (iii) removing the precipitated carbonate or bicarbonate salt from the aqueous solution in step (ii) to result in a solid form of said carbonate or bicarbonate salt of the carbon dioxide complexing compound. The method may further include a step (iv) of regenerating the carbon dioxide complexing compound by subjecting the precipitated salt to sufficient heat and/or vacuum.

23 Claims, 4 Drawing Sheets

(51) Int. Cl.
- *B01D 53/78* (2006.01)
- *B01D 53/96* (2006.01)
- *C07C 279/00* (2006.01)
- *C07C 279/02* (2006.01)
- *C07C 279/12* (2006.01)
- *C07C 279/16* (2006.01)
- *C07C 279/18* (2006.01)

(52) U.S. Cl.
CPC ......... *B01D 2252/2053* (2013.01); *B01D 2252/20415* (2013.01); *B01D 2252/20442* (2013.01); *B01D 2257/504* (2013.01)

(56) References Cited

U.S. PATENT DOCUMENTS

| | | |
|---|---|---|
| 9,260,326 B2 | 2/2016 | Custelcean et al. |
| 2003/0219440 A1 | 11/2003 | Tobia et al. |
| 2012/0027664 A1 | 2/2012 | Pinard Westendorf et al. |
| 2014/0178278 A1 | 6/2014 | Siskin et al. |
| 2017/0014760 A1 | 1/2017 | Stauffer |
| 2017/0081223 A1 | 3/2017 | Hull et al. |
| 2018/0134655 A1 | 5/2018 | Custelcean et al. |

OTHER PUBLICATIONS

Ulrich, P.C., et al. "The Trypanocidal Activity of Various Aromatic Bisguanylhydrazones In Vivo", Drug Development Research, (1982), 2, pp. 219-228.

French, F.A., et al. "Chemotherapy Studies on Transplanted Mouse Tumors", Cancer Research, (1960), 20, pp. 505-538.

Berge, S.M., et al., "Pharmaceutical Salts", Journal of Pharmaceutical Sciences, (1977), vol. 66, pp. 1-19.

Knownium, K. et al., "Novel endotoxin-sequestering compounds with terephthalaldehyde-bis-guanylhydrazone scaffolds", Bioorganic & Medicinal Chemistry Letters, (2006), 16, pp. 1305-1308.

Custelcean R. et al., "Aqueous sulfate separation by crystallization of sulfate-water clusters", Angew. Chem. Int. Ed., (2015), 54, pp. 10525-10529.

Custelcean R. et al., "Aqueous sulfate separation by sequestration of [(SO4)2(H2O)4]4-clusters within highly insoluble imine-linked bis-guanidinium crystals", Chem. Eur. J., (2016), 22, pp. 1997-2003.

U.S. Office Action dated Jun. 13, 2018 issued in U.S. Appl. No. 15/813,557.

* cited by examiner

GUANIDINE COMPOUNDS FOR CARBON DIOXIDE CAPTURE

CROSS REFERENCE TO RELATED APPLICATION

The present application claims benefit of U.S. Provisional Application No. 62/647,052, filed on Mar. 23, 2018 and U.S. Provisional Application No. 62/514,997, filed on Jun. 5, 2017, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention generally relates to methods for capturing and removing carbon dioxide from a gaseous source, such as air, and more specifically, wherein such methods employ guanidine-based compositions.

BACKGROUND OF THE INVENTION

Sustained burning of fossil fuels over the last one and a half centuries has led to an increase in the atmospheric $CO_2$ concentration by more than 45%, from about 280 to over 406 ppm (Earth System Research Laboratory, Global Monitoring Division, NOAA. https://www.esrl.noaa.gov/gmd/ccgg/trends/global.html). As a result, the global temperature now exceeds +1° C. relative to the preindustrial era (Blunden, J. & Arndt, D. S. Eds. State of the climate in 2016. *Bull. Amer. Meteor. Soc.* 98, Si-S277, 2017). In order to meet the goals of the Paris Climate Agreement to limit global warming below 2° C. by the end of this century, an aggressive plan is needed for reducing fossil fuel emissions and gradual decarbonization of the global economy. However, recent studies indicate that might not be sufficient after all, and stabilizing the climate to an optimal level will likely require large-scale deployment of 'negative emissions' technologies (NETs), i.e., removing $CO_2$ from ambient air (Hansen et al. Young people's burden: Requirement of negative $CO_2$ emissions, *Earth Syst. Dynan.* 8, 577-616, 2017). Indeed, as the Earth is out of energy balance with the current atmospheric composition, more warming is expected even if fossil fuel emissions were to suddenly stop (Mauritsen, T. et al., Nature Climate Change DOI:10.1038/nclimate3357, 2017). Furthermore, it has been recently suggested that, ideally, the atmospheric $CO_2$ concentration should be below 350 ppm, to bring the global temperature back within the optimum range of the pre-industrial Holocene period. Meeting this ambitious goal would require the removal of at least 550 Gt $CO_2$ (550 billion tons of $CO_2$) out of the atmosphere by the end of this century (Hansen et al., Ibid.).

Direct air capture (DAC) of carbon dioxide from ambient air by engineered chemical reactions represents a distinct category of NETs among other more "natural" approaches to negative emissions, including bioenergy with carbon capture and storage, afforestation and reforestation, and enhanced weathering of minerals. DAC has the advantage of relatively low land and water requirements, and it has been estimated it could remove up to 12 $GtCO_2$/year (Psarras, P., et al., WIREs Energy Environ 6:e253, DOI: 10.1002/wene.253, 2017). However, living up to such great expectations requires sustained research efforts over the next few decades to improve the existing DAC technologies or develop completely new ones that are economical and can be deployed on a large scale.

The low concentration of $CO_2$ in the air (~400 ppm) and the inherently open nature of the DAC process impose some constraints on the type of sorbents that can be used. First of all, the $CO_2$ binding has to be relatively strong and selective against other atmospheric components (especially water), which automatically disqualifies most physisorbent materials. Toxic and volatile liquid sorbents, such as amines, the workhorse of industrial $CO_2$ scrubbing, are also undesirable due to the negative environmental impact expected from their large-scale deployment in open spaces. To date, there are two classes of sorbents that have been extensively investigated for DAC applications: aqueous alkaline sorbents (i.e., NaOH, KOH, $Ca(OH)_2$) and porous solid-supported amines. The aqueous alkaline sorbents have the advantage of ready availability and relatively fast sorption kinetics, but are highly corrosive and the sorbent regeneration is energy intensive, requiring very high temperatures of ~900° C. Solid-supported amines have lower regeneration energies and temperatures but tend to have slower sorption kinetics and their optimum performance requires maintaining a high surface area over multiple cycles and preventing water condensation in the pores (Wang, T., et al., *Greenhouse Gas Sci. Technol.* 6, 138-149, 2016). They also tend to chemically and thermally degrade over time, especially when heated in open air. A different approach based on anion-exchange resins acting as moisture-swing $CO_2$ absorbents under mild conditions has been demonstrated, although the partial pressure of the released $CO_2$ is relatively low, requiring additional concentration steps before storage (Wang, T., et al., *Environ. Sci. Technol.* 45, 6670-6675 (2011); Wang, T., et al., *Phys. Chem. Chem. Phys.* 15, 504-514, 2013). Thus, there remains a need for developing new technologies that combine the best attributes of liquid and solid sorbents, and that are energy efficient and cost-effective.

SUMMARY OF THE INVENTION

The instant disclosure describes a process for removing carbon dioxide from a gaseous source by first contacting the gaseous source with an aqueous carbon dioxide sorbent (e.g., a metal hydroxide, metal carbonate, or an organoamine, such as an amino acid) that quickly captures large amounts of carbon dioxide from the gaseous source in the form of an aqueous-soluble carbonate or bicarbonate salt, followed by contact and complexation with a specialized bis-iminoguanidine compound, as further discussed below, which results in precipitation of a carbonate or bicarbonate salt of the bis-iminoguanidine compound. The precipitated salt can then conveniently be removed from solution. In preferred embodiments, the precipitated salt is subjected to sufficient heat, preferably by a renewable energy process (e.g., solar heating), to release carbon dioxide gas with simultaneous regeneration of the bis-iminoguanidine compound, wherein the released carbon dioxide gas is either quarantined for storage and/or converted into a useful product.

The carbon dioxide complexing compound (i.e., the specialized bis-iminoguanidine compound), before contact with the aqueous-soluble carbonate or bicarbonate salt formed from the carbon dioxide sorbent, has a structure within the following generic formula:

(1)

where A is a ring-containing moiety or a bond, and wherein one or more of the hydrogen atoms in Formula (1) may be replaced with one, two, or more equivalent number of methyl groups.

The precipitated carbonate or bicarbonate salt containing the specialized bis-iminoguanidine compound may have a structure within the following generic formula:

(1a)

wherein A is as provided above under Formula (1); $X^{m-}$ is a carbonate or bicarbonate anion, with m being 1 for bicarbonate and 2 for carbonate; and n is an integer of 1 or 2; provided that n×m=2.

In particular embodiments, the method for removing carbon dioxide from a gaseous source involves the following steps: (i) contacting the gaseous source with an aqueous solution of a carbon dioxide sorbent that reacts with carbon dioxide to form an aqueous-soluble carbonate or bicarbonate salt of the carbon dioxide sorbent; (ii) contacting the aqueous solution from step (i) with a carbon dioxide complexing compound, which is different from the carbon dioxide sorbent, to result in precipitation of a carbonate or bicarbonate salt of the carbon dioxide complexing compound and regeneration of the carbon dioxide sorbent; and (iii) removing the precipitated carbonate or bicarbonate salt from the aqueous solution in step (ii) to result in a solid form of the carbonate or bicarbonate salt of the carbon dioxide complexing compound. The method may further include: (iv) regenerating the carbon dioxide complexing compound by subjecting the carbonate or bicarbonate salt of the carbon dioxide complexing compound to heat sufficient to result in release of carbon dioxide gas emanating from the carbonate or bicarbonate salt of the carbon dioxide complexing compound along with simultaneous restoration of the carbon dioxide complexing compound, wherein the released carbon dioxide gas is either quarantined for storage and/or converted into a useful product.

In particular embodiments, the gaseous source is contacted intimately with the aqueous solution of the carbon dioxide sorbent by use of an air-liquid contact facilitator, wherein the air-liquid contact facilitator increases the surface area of the aqueous solution containing the carbon dioxide sorbent to increase the air-liquid contact area between the gaseous source and the aqueous solution containing the carbon dioxide sorbent. In further particular embodiments, the air-liquid contact facilitator is a humidifying device that contains a reservoir of the aqueous solution containing the carbon dioxide sorbent, and the humidifying device increases the surface area of the aqueous solution by wicking the aqueous solution or forming a mist of the aqueous solution.

BRIEF DESCRIPTION OF THE DRAWINGS

FIGS. 2A, 2B.

FIGS. 4A, 4B.

DETAILED DESCRIPTION OF THE INVENTION

In the method for removing carbon dioxide, a gaseous source containing carbon dioxide is contacted with an aqueous solution of a carbon dioxide ($CO_2$) sorbent that reacts with carbon dioxide to form an aqueous-soluble carbonate or bicarbonate salt of the carbon dioxide sorbent. The foregoing step can herein be referred to as a first step, i.e., step (i). The gaseous source can be any volume of gas containing carbon dioxide. The gaseous source can be, for example, air, waste gas from an industrial or commercial process, flue gas from a power plant, exhaust from an engine, or sewage or landfill gas. The term "aqueous," as used herein, refers to the presence of water. In some embodiments, the only liquid in the solution is water, while in other embodiments, the liquid in the solution may be water in admixture with a water-soluble organic solvent, such as an alcohol, acetone, or tetrahydrofuran. The $CO_2$ sorbent may be, for example, one or more organoamines, alkali hydroxides (e.g., NaOH or KOH), alkali carbonates (e.g., $Na_2CO_3$ or $K_2CO_3$), and/or alkaline earth hydroxides (e.g., $Ca(OH)_2$). The organoamines may be primary or secondary amines. Some examples of conventional organoamines include methylamine, ethylamine, ethylenediamine, and ethanolamine. As well known, organoamines react with carbon dioxide to form ammonium bicarbonates and ammonium carbonates. As is also well known, metal hydroxides react with carbon dioxide to form metal bicarbonates and carbonates; and metal carbonates react with carbon dioxide to form metal bicarbonates. In some embodiments, any one or more of the above carbon dioxide sorbents is excluded. The carbon dioxide sorbent can be present in any suitable concentration in the aqueous solution, e.g., 0.1, 0.2, 0.5, 1, 1.5, 2, 2.5, 3, 4, or 5 M concentration, or a saturated concentration, or a concentration within a range bounded by any two of the foregoing values.

In particular embodiments, the one or more organoamines are selected from one or more amino acids. Any amino acid, which includes natural and non-natural amino acids, should be capable of functioning as a carbon dioxide sorbent, although some amino acids may function better than others. The amino acid may be an alpha- or beta-amino acid, or a derivative or mimic of an amino acid (e.g., taurine). Some examples of suitable amino acids include glycine, sarcosine, alanine, beta-alanine (3-aminopropanoic acid), valine, leucine, isoleucine, serine, threonine, glutamine, asparagine, glutamic acid, aspartic acid, lysine, histidine, arginine, phenylalanine, tyrosine, proline, and tryptophan, and N-alkyl derivatives, ester derivatives, or salts of any of the foregoing amino acids. In some embodiments, the amino acid is selected from glycine and/or N-alkylglycines, wherein the alkyl group is independently selected from hydrocarbon groups containing 1-6 carbon atoms (e.g., methyl, ethyl, n-propyl, isopropyl, n-butyl, isobutyl, sec-butyl, t-butyl, n-pentyl, isopentyl, n-hexyl, and isohexyl). Some examples of N-alkylglycines include sarcosine (where the N-alkyl group is methyl) and N-methylalanine. For purposes of the present invention, the amino acid or other organoamine should possess at least one NH group.

In some embodiments, the gaseous source is contacted intimately with the aqueous solution containing the carbon dioxide sorbent by use of an air-liquid contact facilitator. The air-liquid contact facilitator functions by increasing the contact surface area between the gaseous source and the aqueous solution. The air-liquid contact facilitator typically achieves this by increasing the surface area of the aqueous solution containing the carbon dioxide sorbent. Numerous methods are available for increasing the surface area of an aqueous solution, all of which are considered herein. The air-liquid contact facilitator may increase the solution surface area by, for example, spreading the solution onto an absorbent material (e.g., a wick), which the solution spreads into by capillary action. Alternatively, for example, the air-liquid contact facilitator may increase the solution surface area by forming a mist (i.e., aerosol) of the solution. In some embodiments, the surface area of the gas may be increased to increase the contact surface area between the gas and the solution. For example, the gaseous source may be bubbled through the sorbent solution, along with optional agitation (e.g., stirring) of the solution. Regardless of the process used for increasing the surface area of the solution, the result is an increased area of contact between the sorbent-containing solution and the carbon dioxide-containing gaseous source.

In particular embodiments, the air-liquid contact facilitator is a humidifying device that contains a reservoir of the aqueous solution containing the carbon dioxide sorbent, and the humidifying device increases the surface area of the aqueous solution by wicking the aqueous solution or forming a mist of the aqueous solution. As the reservoir is in contact with the increased surface area part of the solution (e.g., wicked solution or solution mist), the reservoir will accumulate the resulting aqueous-soluble carbonate or bicarbonate salt of the carbon dioxide sorbent over time.

Generally, water and/or other solvent in the aqueous solution is lost over time due to evaporation, and this gradually increases the concentration of the carbon dioxide sorbent. This occurs at a faster rate when an air-liquid contact facilitator is used. Thus, to maintain a precise or approximate concentration of the carbon dioxide sorbent over time, a feature may be included whereby an amount of water and/or other solvent is added over time to precisely or approximately replenish the amount of water and/or other solvent that has been lost over the same period of time.

After the carbon dioxide sorbent forms the aqueous-soluble carbonate or bicarbonate salt in step (i), the aqueous solution from step (i) is contacted with a carbon dioxide complexing compound, which is different from the carbon dioxide sorbent and has a bis-iminoguanidine ("BIG") structure according to Formula (1), as provided above. The foregoing contacting step can herein be referred to as a second step, i.e., step (ii). The term "contacting" refers to contact on a molecular level. The term "carbon dioxide complexing compound" refers to the ability of the bis-iminoguanidine compound to complex with the carbonate or bicarbonate anion and form a precipitate salt (i.e., aqueous-insoluble salt) with the carbonate or bicarbonate anion. When the carbon dioxide complexing compound forms the insoluble carbonate or bicarbonate salt, it simultaneously regenerates the carbon dioxide sorbent by abstracting protons from the carbon dioxide sorbent in the aqueous-soluble salt, thereby forming the bis-iminoguanidinium ($BIGH_2^+$) salt structure according to Formula (1a), as provided above. Any suitable method for molecularly contacting the carbon dioxide complexing compound with the aqueous solution is considered herein. For example, in some embodiments, the carbon dioxide complexing compound is added to the aqueous solution directly as a solid, at which time the carbon dioxide complexing compound at least partially dissolves into the aqueous solution before precipitating as an insoluble carbonate or bicarbonate salt. In other embodiments, the carbon dioxide complexing compound is added as a premade aqueous solution or suspension to the aqueous solution containing the aqueous-soluble carbonate or bicarbonate salt. In some embodiments, the precipitated bis-iminoguanidinium salt is crystalline (e.g., monocrystalline or polycrystalline), while in other embodiments, the salt is amorphous.

The bis-iminoguanidine compound that herein functions as a carbon dioxide complexing compound in step (ii) has a structure within the scope of the following generic structure:

(1)

12qAs further discussed below, the variable A is either a ring-containing moiety or a bond. Although Formula (1) depicts a specific tautomeric arrangement, Formula (1) is intended to include any other tautomers that can be derived from or interconvert with the tautomer shown in Formula (1). As well known, tautomeric structures have the same atomic connections (aside from one or more protons) but differ in the placement of double bonds, generally with concomitant relocation of one or more protons. Some examples of tautomers of Formula (1) are provided as follows:

(1-1)

(1-2)

In a first embodiment, the variable A in Formula (1) is a bond. In that case, the compound under Formula (1) can correspond to the following exemplary structures (along with optional replacement of one, two, or more hydrogen atoms with an equivalent number of methyl groups):

(1-3)

(1-3')

In a second set of embodiments, the variable A is a ring-containing moiety. The ring-containing moiety may be or include a ring (i.e., a cyclic group). The ring-containing moiety (A) is or includes any cyclic group that includes at least one, two, three, or four carbon ring atoms. Since the cyclic group is attached to two iminoguanidine groups, the cyclic group in the ring-containing moiety (A) necessarily includes two sites engaged in bonds, either directly, or indirectly via a linker, to the iminoguanidine groups. Typically, the two sites in the ring (A) linked, directly or indirectly, to the iminoguanidine groups are ring carbon atoms. In some embodiments, the ring-containing moiety is or includes a monocyclic ring, i.e., a single ring not bound or fused to another ring. In other embodiments, the ring-containing moiety is or includes a ring system, wherein the term "ring system" refers to a polycyclic moiety (e.g., a bicyclic or tricyclic moiety). The cyclic group can be polycyclic by either possessing a bond between at least two rings or a shared (i.e., fused) bond between at least two rings. The one or more rings in the ring-containing moiety is typically a five-membered, six-membered, or seven-membered ring.

In one set of embodiments, the ring-containing moiety (A) is or includes a carbocyclic ring or ring system. The term "carbocyclic" indicates that the ring or ring system contains only carbon ring atoms. The carbocyclic ring or ring system can be saturated or unsaturated. Some examples of carbocyclic rings that are monocyclic and saturated include cyclopentyl, cyclohexyl, and cycloheptyl rings. Some examples of carbocyclic rings that are monocyclic and unsaturated (which may be aliphatic or aromatic) include cyclopentenyl, cyclopentadienyl, cyclohexenyl, cyclohexadienyl, cyclo- heptenyl, cycloheptadienyl, and phenylene (benzene) rings. Some examples of carbocyclic rings that are polycyclic and saturated include decalin, norbornane, bicyclohexane, and 1,2-dicyclohexylethane ring systems. Some examples of carbocyclic rings that are polycyclic and unsaturated include naphthalene, anthracene, phenanthrene, phenalene, and indene ring systems.

In another set of embodiments, the ring-containing moiety (A) is or includes a heterocyclic ring or ring system. The term "heterocyclic" indicates that the ring or ring system contains at least one ring heteroatom. The ring heteroatom is typically selected from nitrogen, oxygen, and sulfur. The heterocyclic ring or ring system can be saturated or unsaturated. Some examples of heterocyclic saturated rings or ring systems include those containing at least one ring nitrogen atom (e.g., pyrrolidine, piperidine, piperazine, imidazolidine, azepane, and decahydroquinoline rings); those containing at least one ring oxygen atom (e.g., oxetane, tetrahydrofuran, tetrahydropyran, 1,4-dioxane, 1,3-dioxane, and 1,3-dioxepane rings); those containing at least one ring sulfur atom (e.g., tetrahydrothiophene, tetrahydrothiopyran, 1,4-dithiane, 1,3-dithiane, and 1,3-dithiolane rings); those containing at least one ring oxygen atom and at least one ring nitrogen atom (e.g., morpholine and oxazolidine rings); and those containing at least one ring nitrogen atom and at least one ring sulfur atom (e.g., thiazolidine and thiamorpholine rings). Some examples of heterocyclic unsaturated rings or ring systems include those containing at least one ring nitrogen atom (e.g., pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, and 1,8-naphthyridine rings); those containing at least one ring oxygen atom (e.g., furan, pyran, 1,4-dioxin, benzofuran, dibenzofuran, and dibenzodioxin); those containing at least one ring sulfur atom (e.g., thiophene, thianaphthene, benzothiophene, thiochroman, and thiochromene rings); those containing at least one ring oxygen atom and at least one ring nitrogen atom (e.g., oxazole, isoxazole, benzoxazole, benzisoxazole, oxazoline, 1,2,5-oxadiazole (furazan), and 1,3,4-oxadiazole rings); and those containing at least one ring nitrogen atom and at least one ring sulfur atom (e.g., thiazole, isothiazole, benzothiazole, benzoisothiazole, thiazoline, and 1,3,4-thiadiazole rings).

In the event that the variable A is a ring, Formula (1) and sub-formulas are intended to include any regioisomers that may differ in the connection points of the two iminoguanidine groups on the ring-containing moiety (A). Thus, as an example, if A is taken as a benzene (phenylene) ring, the two shown iminoguanidine groups may be located at the 1,4 (para), 1,3 (meta) or 1,2 (ortho) positions. In some embodiments, the iminoguanidine groups are located the farthest from each other on the ring-containing moiety. In the case of a benzene ring, the farthest positions correspond to the 1,4 (para) positions. In the event that the structure according to Formula (1) possesses one or more stereocenters, Formula (1) is intended to include all resulting stereoisomers. The stereoisomer may include one or more enantiomers and/or diastereomers.

Some examples of compounds according to Formula (1) in which A is a ring-containing moiety include the following:

In step (ii), when the bis-iminoguanidine molecule according to Formula (1) or sub-formula thereof contacts the aqueous solution from step (i), an aqueous-insoluble salt forms, which includes a mono-protonated (mono-cationic) or di-protonated (bi-cationic) form of the bis-iminoguanidine molecule complexed with carbonate or bicarbonate. At the same time, the carbon dioxide sorbent is regenerated, as discussed above. In the case of the di-protonated form of the bis-iminoguanidine molecule, the salt form of Formula (1) can be expressed by the following generic structure:

In the case of the mono-protonated form of the bis-iminoguanidine molecule, the salt form of Formula (1) can be expressed by the following generic structure:

As the structure in Formula (1a) or (1a') derives directly from Formula (1), it is understood that Formula (1a) or (1a'), like Formula (1), includes all possible tautomers, regioisomers, and stereoisomers described above for Formula (1). Thus, the positive charge shown in Formula (1a) or (1a') may be located on any of the other nitrogen atoms through tautomerizaton. As well known in the case of tautomers, the positive charge is generally distributed among all atoms capable of holding a positive charge in the various tautomers. Likewise, it is well known that partial double bond character is generally present among all of the bonds capable of engaging in double bonds in the various tautomers. Moreover, the structures in Formulas (1), (1a), and (1a') include the possibility of one or more of the hydrogen atoms in Formula (1), (1a), or (1a'), whether the hydrogen atoms are shown or not shown in the formula, being replaced with one or more methyl groups, respectively.

In Formula (1a) or (1a'), $X^{m-}$ is a carbonate or bicarbonate anion, with m being 1 for bicarbonate and 2 for carbonate. In the case of the bis-iminoguanidine molecule being di-protonated, the variable n is an integer of 1 or 2, provided that n multiplied by m is 2 (i.e., n×m=2) to counterbalance the +2 charge of the di-protonated bis-iminoguanidinium species. In the case of the bis-iminoguanidine molecule being mono-protonated, the variable n is 0.5 or 1, provided that n multiplied by m is 1 (i.e., n×m=1) to counterbalance the +1 charge of the mono-protonated bis-iminoguanidinium species.

When the variable A in Formula (1) is a bond, the variable A in Formula (1a) or (1a') will necessarily also be a bond. In that case, the compound under Formula (1a) has the following structure:

(1a-1)

When the variable A in Formula (1) is a ring-containing moiety, the variable A in Formula (1a) or (1a') will necessarily also be the same ring-containing moiety. Some examples of compounds according to Formula (1a) include the following:

(1a-2)

(1a-3)

(1a-4)

(1a-5)

(1a-6)

(1a-7)

(1a-8)

(1a-9)

(1a-10)

(1a-11)

(1a-12)

(1a-13)

As further discussed below, any of the above exemplary compounds under Formula (1a) or (1a') may be converted to the respective neutral analogue according to Formula (1) by removal of the one or two protons located on the one or two positively charged amine groups. Moreover, in compounds under Formula (1), (1a), or (1a') where A is a ring containing an —NH— group in the ring, the hydrogen atom on the ring nitrogen atom may (optionally) be replaced with a hydrocarbon group, such as a methyl, ethyl, n-propyl, isopropyl, n-butyl, isobutyl, sec-butyl, t-butyl, phenyl, or benzyl group.

As also provided above, one or more of the hydrogen atoms in any of the above exemplary structures, whether the hydrogen atoms are shown or not shown, may be replaced with one, two, or more methyl groups, respectively. In the event of one or more hydrogen atoms being replaced with a methyl or other hydrocarbon group, the substitution in the structure of neutral compounds under Formula (1) should not result in substantial insolubility of the neutral compound in the aqueous solution containing the sorbent. If necessary, the aqueous solution may be heated to a mild temperature (e.g., 40 or 50° C.) to aid in solubilization of the neutral compound. An aqueous-soluble organic solvent may also be added to improve the solubility of the neutral compound.

After the carbonate or bicarbonate salt is precipitated from the aqueous solution in step (ii), the precipitate is removed (separated) from the aqueous solution to result in a solid form of the carbonate or bicarbonate salt precipitated from step (ii). The foregoing salt removal step may herein be referred to as the third step, i.e., step (iii). Generally, the precipitated salt is filtered from the solution. If desired, the isolated salt may be rinsed and/or dried. The filtered solution is generally re-used, since it contains the regenerated carbon dioxide sorbent.

After removing the salt in step (iii), the method may further include a step of regenerating (restoring) the neutral bis-iminoguanidine carbon dioxide complexing compound of Formula (1) while at the same time releasing carbon dioxide gas by decomposition of the bicarbonate or carbonate species in the salt. The foregoing step may herein be referred to as a fourth step, i.e., "step (iv)". In particular embodiments, the bis-iminoguanidinium salt removed in step (iii) is subjected to heat, or vacuum, or both (heat and vacuum), sufficient to result in release of carbon dioxide gas from the salt while at the same time (i.e., simultaneously) regenerating the neutral form of the bis-iminoguanidine compound of Formula (1). The carbon dioxide that has been released can be either quarantined for storage for an unspecified amount of time or until it is used in another process, or the released carbon dioxide gas may be directly used in a process or converted to a useful chemical substance or feedstock as the carbon dioxide is released. In some embodiments, the evolved carbon dioxide gas is stored and/or pressurized, as appropriate, and may be subsequently further processed or reacted in an industrial or commercial process. The carbon dioxide may be conveyed to a process where the carbon dioxide is converted to, for example, dry ice, a hydrocarbon fuel, methanol, or ethanol.

If a vacuum is applied, the regeneration step may be conducted at ambient (room) temperature, e.g., 20° C., 25° C., or 30° C. Generally, the greater the vacuum, the lower the temperature that can successfully achieve the regeneration step. Depending on the amount of vacuum being applied, the salt in step (iii) may be heated to a temperature of at least or above 40° C., 50° C., or 60° C. and up to or below 160° C., 180° C., 200° C., 220° C., or 250° C. to effect the release of carbon dioxide and regeneration of the carbon dioxide complexing compound. In different embodiments, the temperature used in step (iii) is precisely or about, for example, 40° C., 50° C., 60° C., 70° C., 80° C., 90° C., 100° C., 110° C., 120° C., 130° C., 140° C., 150° C., 160° C., 170° C., 180° C., 190° C., 200° C., 220° C., or 250° C. or a temperature within a range bounded by any two of the foregoing values, such as 20-250° C., 30-250° C., 40-250° C., 40-180° C., 40-160° C., 40-120° C., 60-160° C., 60-140° C., 60-120° C., 60-100° C., 60-90° C., 60-80° C., 70-160° C., 70-140° C., 70-120° C., 70-100° C., 80-160° C., 80-140° C., 80-120° C., or 80-100° C.

In some embodiments, the bis-iminoguanidinium salt in step (iii) is heated by use of a renewable energy source, which may be practiced with or without a vacuum. The renewable energy source may be, for example, solar energy. In one embodiment, the solar energy is used for direct heating, such as in a solar heat concentrator (e.g., a solar oven). In another embodiments, the solar energy is used for indirect heating, such as by converting the solar energy to electricity or hydrogen, which is then used to power a heating device. Alternatively, direct or indirect solar energy may be used to heat water to steam, and the bis-iminoguanidinium salt in step (iii) is heated with the steam. Hydrogen may be used directly as a fuel, or indirectly in a fuel cell to produce electricity. Other forms of renewable energy (e.g., wind or hydroelectric power) may be used to produce electricity or hydrogen to power a heating device. Geothermal power may also be used directly or indirectly to heat the salt in step (iii). In some embodiments, a manmade heating process that employs a fuel that emits carbon dioxide when combusted is excluded in step (iii).

The compounds according to Formula (1) can be synthesized by methods well known in the art. In particular embodiments, a compounds according to Formula (1) is synthesized by reacting aminoguanidine (or a methylated derivative thereof) with a ring-containing dialdehyde or diketone under conditions where an imine linkage is formed between an amino group on the aminoguanidine and the carbon of the aldehyde or ketone group. The ring-containing dialdehyde or diketone includes a ring-containing moiety (A), as described above. A general schematic of the process is provided as follows:

In the above scheme, A is a ring-containing moiety, as described above. The group R is typically hydrogen (which corresponds to a dialdehyde reactant), but R may be a hydrocarbon group, particularly a hydrocarbon group containing 1-6, 1-7, or 1-8 carbon atoms, such as methyl, ethyl, n-propyl, isopropyl, n-butyl, isobutyl, sec-butyl, t-butyl, phenyl, or benzyl group, which corresponds to a diketone reactant. The above scheme is for directly producing a neutral bis-iminoguanidine compound according to Formula (1). Alternatively, by reacting the aldehyde or ketone with a guanidinium compound, a guanidinium salt can be produced and converted to the neutral guanidine compound by reaction with a base. Moreover, any one or more hydrogen atoms of the aminoguanidine or aminoguanidinium reactant may be replaced with one or more methyl groups, respectively, except that the aminoguanidine or aminoguanidinium reactant should retain at least one primary amine group for reaction with the dialdehyde or diketone. Alternatively, one or more hydrogen atoms of the bis-iminoguanidinium or bis-iminoguanidine product may be replaced with one or more methyl groups by, for example, reaction with methyl iodide.

Examples have been set forth below for the purpose of illustration and to describe certain specific embodiments of the invention. However, the scope of this invention is not to be in any way limited by the examples set forth herein.

Examples

Synthesis of 2,6-pyridine-bis(iminoguanidine) (PyBIG)

PyBIG

The PyBIG compound was synthesized according to a previously reported method, which was scaled up and optimized (see C. A. Seipp et al., *Angew. Chem. Int. Ed.* 56, 1042-1045, 2017). The details of the synthesis are as follows:

Pyridine-2,6-dicarbaldehyde: A mixture of pyridine-2,6-dimethanol (10.00 g, 71.86 mmol) and Dess-Martin periodinane (67.06 g, 158.10 mmol) were suspended in 400 mL of dichloromethane. The reaction mixture was stirred at room temperature for 12 hours. Subsequently, 100 mL of water was added to the reaction and the mixture was stirred at room temperature for an additional 12 hours. A 300 mL 50/50 mixture of saturated $NaHCO_3$ and 10% $Na_2S_2O_3$ was added to the reaction mixture and stirred for two additional hours, and then the mixture was filtered through a celite plug. The filtrate was poured into a separatory funnel and the organic layer was collected, washed with brine, and dried with $Na_2SO_4$. The dichloromethane was removed under vacuum resulting in a white-yellow solid. The product was purified by column chromatography by partly dissolving the product in hexanes and loading it onto a silica gel column (Note: the solid is not fully soluble in hexanes), and eluting it using a hexanes-ethyl acetate solvent system (7:3 hexanes/ethyl acetate). The final product was isolated as a white solid. Yield: 7.64 g, 78.7%. $_1$H NMR (400 MHz, $CDCl_3$) δ 10.136 (2H, s), 8.164 (2H, d), 8.070 (1H, t). $^{13}$C NMR (100 MHz, $CDCl_3$) δ 192.38, 152.99, 138.43, 125.36.

Direct Air Capture (DAC) of Carbon Dioxide

Figure 1:
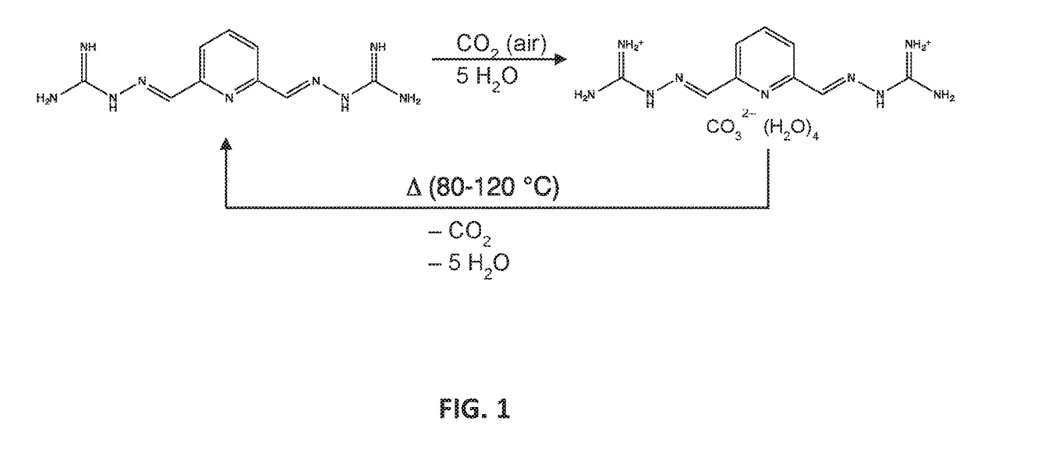
FIG. 1. Schematic diagram showing $CO_2$ capture from ambient air with aqueous PyBIG, leading to crystallization of $PyBIGH_2(CO_3)(H_2O)_4$. The $CO_2$ is released, and the PyBIG compound is regenerated quantitatively by relatively mild heating of the carbonate crystals.

Preliminary results indicated that aqueous 2,6-pyridine-bis(iminoguanidine) (PyBIG) captures $CO_2$ from ambient air and binds it as a crystalline tetrahydrated carbonate salt $PyBIGH_2(CO_3)(H_2O)_4$. The $CO_2$ can be released by heating the carbonate crystals at relatively mild temperatures of 80-120° C., which regenerates the PyBIG compound quantitatively. A general schematic of the process is shown in FIG. 1.

Examination of the $PyBIGH_2(CO_3)(H_2O)_4$ crystals by optical microscopy revealed that, upon heating in an oven at 120° C. for one hour, the crystals changed their color from cream to yellow to opaque. Thermogravimetric analysis coupled with mass spectrometry (TGA-MS) provided a more quantitative picture of the decomposition process. In a temperature-ramped TGA measurement, the $PyBIGH_2(CO_3)(H_2O)_4$ crystals lost 35.2% of their mass between 65 and 140° C., and the MS analysis confirmed the simultaneous evolution of water and $CO_2$. These measurements are consistent with the loss of one carbonate and two protons (as $CO_2$ and $H_2O$), and four additional water molecules, as expected from the crystal structure of $PyBIGH_2(CO_3)(H_2O)_4$ (35.1% theoretical mass loss). Similarly, the mass loss of the crystals heated in the oven for one hour at 120° C. (vide supra) was 34.3%, and the FTIR and NMR spectroscopic analysis of the resulting solid confirmed the complete disappearance of the carbonate peak and the regeneration of the anhydrous PyBIG compound. The TGA-MS analysis showed no decomposition of the regenerated compound up to 190° C., which provides a thermal stability window of at least 50° C. for compound recovery. Isothermal TGA runs at 120 and 100° C. showed complete loss of carbon dioxide and water after 60 and 150 minutes, respectively, with no additional mass loss after 5 hours. On the other hand, at 80° C. the decomposition reached 77% completion after 300 minutes. This corresponds to about an order of magnitude reduction in the decomposition temperature compared to inorganic carbonates, such as $Na_2CO_3$ or $CaCO_3$, involved in traditional DAC technologies.

The elementary steps involved in the $CO_2$ absorption and the overall reaction are represented by equations 1-7 as follows:

$$PyBIG_{(s)} \rightleftharpoons PyBIG_{(aq)} \tag{1}$$

$$PyBIG_{(aq)} + 2H_2O \rightleftharpoons PyBIGH_2^{2+}{}_{(aq)} + 2HO^-{}_{(aq)} \tag{2}$$

$$CO_{2(g)} \rightleftharpoons CO_{2(aq)} \tag{3}$$

$$CO_{2(aq)} + HO^-{}_{(aq)} \rightleftharpoons HCO_3^-{}_{(aq)} \tag{4}$$

$$HCO_3^-{}_{(aq)} + HO^-{}_{(aq)} \rightleftharpoons CO_3^{2-}{}_{(aq)} + H_2O \tag{5}$$

$$PyBIGH_2^{2+}{}_{(aq)} + CO_3^{2-}{}_{(aq)} + 4H_2O \rightleftharpoons PyBIGH_2(CO_3)(H_2O)_{4(s)} \tag{6}$$

$$PyBIG_{(s)} + CO_{2(g)} + 5H_2O \rightarrow PyBIGH_2(CO_3)(H_2O)_{4(s)} \tag{7}$$

The crystalline PyBIG compound (as PyBIG.2H2O hydrate) first dissolves into water (equation 1), then the two guanidine groups become protonated by water molecules, generating the dicationic form of the compound ($PyBIGH_2^{2+}$) and $HO^-$ (equation 2). The hydroxide anions are the actual active species that react with the $CO_2$ absorbed from air (equation 3) and generate bicarbonate (equation 4) and carbonate anions (equation 5). Finally, the $PyBIGH_2^{2+}$ and $CO_3^{2-}$ ions crystallize with water into crystalline $PyBIGH_2(CO_3)(H_2O)_4$ (equation 6). The net reaction, shown in equation 7, corresponds to crystalline PyBIG converting into crystalline $PyBIGH_2(CO_3)(H_2O)_4$, in the presence of $CO_2$ and water, through dissolution/recrystallization.

Although PyBIG can capture $CO_2$ from ambient air according to equation 7, the reaction is too slow for practical considerations. The kinetics of $CO_2$ absorption by PYBIG is limited by a number of factors. First, the atmospheric $CO_2$ concentration is very low (~0.04%). For aqueous alkaline solutions, such as NaOH, the absorption rate has been found to be limited by a combination of the $CO_2$ diffusion into the aqueous solution (equation 3), and the reaction of $CO_2$ with HO— (equation 4). Thus, the rate of $CO_2$ absorption is controlled by the surface area of the air-liquid interface, and the solution alkalinity. For a typical 1 M solution of NaOH, the flux of $CO_2$ absorbed from air has been estimated around 30 µmol/m$^2$/s (Zeman, F., *Environ. Sci. Technol.* 41, 7558-7563, 2007). However, compared to NaOH, PyBIG is significantly less alkaline. The relatively low aqueous solubility of PyBIG (~10 mM) further limits the solution alkalinity, and therefore, the reaction rate with $CO_2$. Thus, a saturated solution of PyBIG (~10 mM) has a pH of about 10, which corresponds to a rate of $CO_2$ reaction that is at least a couple orders of magnitude lower than for NaOH. Another constraint is that in a typical crystallization set-up the air-liquid contact area is relatively small, which further limits the $CO_2$ absorption rate.

Figure 2A:
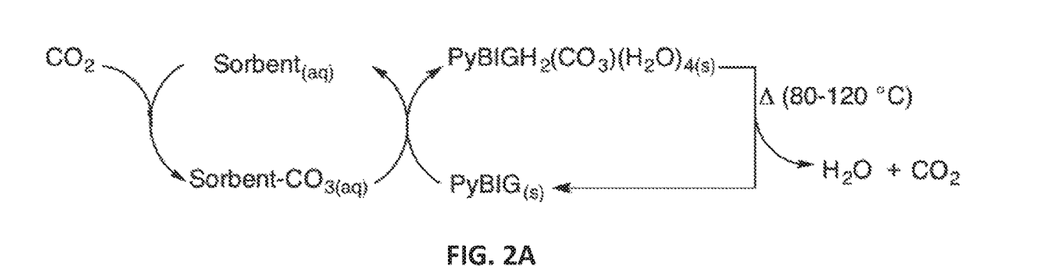
FIG. 2A: General schematic showing a direct air capture (DAC) cycle combining $CO_2$ absorption by an aqueous sorbent, crystallization of $PyBIGH_2(CO_3)$ $(H_2O)_4$ and sorbent regeneration, and $CO_2$ release and PyBIG regeneration by heating of the carbonate crystals.
Figure 2B:
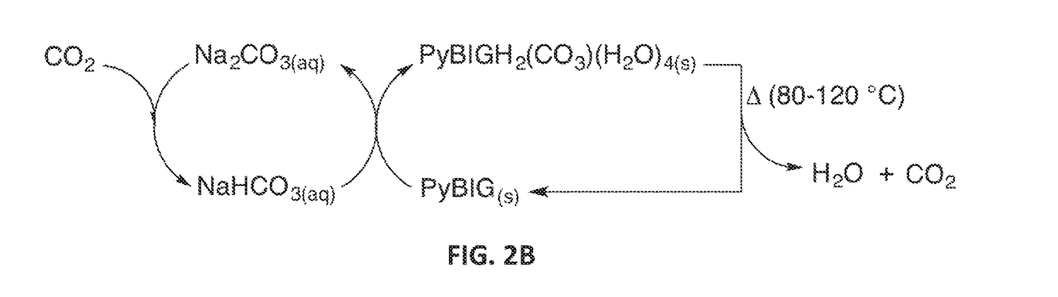
FIG. 2B: Schematic diagram analogous to FIG. 2A, in the particular case where the aqueous sorbent is an alkali carbonate (in particular, sodium carbonate).

In an effort to boost the efficiency of the process, the PyBIG crystallization process was combined with a traditional aqueous sorbent that absorbs atmospheric $CO_2$ relatively fast and converts it into carbonate. Specifically, the initial carbonate-loaded solution was reacted with PyBIG to crystallize $PyBIGH_2(CO_3)(H_2O)_4$ and regenerate the sorbent. Finally, the carbonate crystals were filtered out of solution and heated in the solid state to release the $CO_2$ and regenerate the PyBIG compound, which can then be re-used in another cycle. FIG. 2A provides a general schematic of the above concept. FIG. 2B shows an analogous process where a bicarbonate salt results from reaction of a carbonate salt with carbon dioxide and water. The advantage of such a hybrid approach to $CO_2$ capture, which combines room temperature absorption in the liquid phase with $CO_2$ release in the solid state, is that it benefits from the fast sorption kinetics of an aqueous sorbent while avoiding the energy penalty associated with heating aqueous solutions during regeneration. Furthermore, sorbent loss through evaporation and thermal degradation is minimized.

One approach to DAC with PyBIG is to combine the crystallization of $PyBIGH_2(CO_3)(H_2O)_4$ with the well-established carbonate/bicarbonate $CO_2$ capture cycle. A general schematic of the process is shown in FIG. 2B. The chemical reactions occurring in the carbonate/bicarbonate $CO_2$ capture cycle are shown in the following equations:

$$CO_3^{2-}+CO_3+H_2O \rightarrow 2HCO_3^- \quad \text{(Eq. 1)}$$

$$PyBIG_{(s)}+2HCO_3^-+4H_2O \rightarrow PyBIGH_2(CO_3)(H_2O)_{4(s)}+CO_3^{2-} \quad \text{(Eq. 2)}$$

In this approach, $CO_2$ sorption by an alkali carbonate solution (Eq. 1) is followed by the reaction of the resulting bicarbonate with PyBIG to crystallize $PyBIGH_2(CO_3)(H_2O)_4$ and regenerate the carbonate sorbent (Eq. 2). Finally, thermal decomposition of $PyBIGH_2(CO_3)(H_2O)_4$ regenerates the PyBIG compound and releases the $CO_2$. To demonstrate the feasibility of this approach, solid PyBIG (1 mol equiv) was suspended in a solution of 1 M $NaHCO_3$ (5-6 mol equiv) and the slurry was stirred at room temperature for four hours. The resulting mixture was filtered, and the separated crystalline solid was confirmed by PXRD and FTIR to be $PyBIGH_2(CO_3)(H_2O)_4$. Subsequent heating of the carbonate crystals in the oven for one hour at 120° C. regenerated the PyBIG solid, which was recycled back into the original sodium bicarbonate solution. The entire carbonate separation cycle was run three times, with observed yields for $PyBIGH_2(CO_3)(H_2O)_4$ crystallization of 99.0±0.4%, 97.2±0.6%, and 91.4±0.4%, corresponding to the first, second, and third cycle, respectively. The regeneration of the PyBIG compound was nearly quantitative in each cycle. The slight decrease in the crystallization yield observed in the later cycles is explained by the gradual increase in the solution alkalinity (initial pH 8.5, final pH 10.5) as a result of the increasing $CO_3^{2-}/HCO_3^-$ ratio. As more bicarbonate is converted into carbonate in each subsequent cycle, according to Eq. 2, the pH of the solution should eventually become high enough to inhibit the protonation of PyBIG, thereby decreasing the driving force for the crystallization of $PyBIGH_2(CO_3)(H_2O)_4$. This is corroborated by the FTIR analysis of the isolated solid, which showed preponderantly the carbonate phase after the first two cycles, but a mixture of carbonate and free PyBIG compound after the third cycle.

After considering several potential sorbents, two simple amino acids, glycine and sarcosine, were selected for the DAC system. Aqueous amino acids have a number of positive attributes that make them promising candidates for DAC. They have fast $CO_2$ sorption kinetics, on par with or surpassing more traditional sorbents like monoethanolamine or NaOH. Amino acids are non-volatile, non-corrosive, environmentally friendly, and relatively inexpensive. They are also less susceptible to oxidation than amines. While amino acid sorbents have been employed in $CO_2$ scrubbing from flue gas, their use in DAC remains largely unexplored. The chemical reactions involved in the $CO_2$ absorption with amino acids and in the sorbent regeneration with PyBIG are depicted in equations 8-10 below, with glycine being a representative example.

(8)

(9)

(10)

First, the anionic form of glycine (glycinate) reacts with $CO_2$ and generates the corresponding carbamic acid, which is deprotonated by a second equivalent of glycine to generate the carbamate and the zwitterionic glycine (equation 8). The carbamate is subsequently hydrolyzed to glycinate and bicarbonate (equation 9). Finally, PyBIG takes two protons and a carbonate anion from solution and crystallizes as $PyBIGH_2(CO_3)(H_2O)_4$ (equation 10), which in the process leads to deprotonation of the zwitterionic glycine and regeneration of the glycinate sorbent (normally the two protons are abstracted from bicarbonate and the zwitterion). Notably, adding the three reactions together leads to the same overall reaction represented by equation 7. However, the kinetics of the amino acid-mediated DAC process are expected to be significantly faster than with PyBIG alone.

In addition to fast kinetics for the $CO_2$ reaction with the sorbent, a practical DAC system requires effective mass transfer of $CO_2$ from air into the sorbent solution, which in turn requires an efficient contactor that maximizes the air-liquid interfacial area. Unlike $CO_2$ capture from flue gas, which is typically done in a pressurized absorption column that is designed to operate at high liquid/gas ratios and with a high degree of $CO_2$ removal, DAC is more suitably done in a more open system with contactors that are optimized to ingest large volumes of ambient air, in many ways similar in design with large-scale cooling towers. For the purpose of this study, which is a small-scale proof of principle for DAC with the amino acid/guanidine system, a household humidifier was used as an air-liquid contactor. Like a cooling tower, an air humidifier is designed to maximize the air-water contact area, and by replacing the water with an amino acid solution, it effectively becomes a DAC absorber.

For the direct air capture of $CO_2$ with glycine and sarcosine, the $CO_2$ absorption from air was carried out with an Envion Humidiheat™ household air humidifier. The humidifier consists of a reservoir with a capacity of ~2 L, a rotating wick, which is made of a porous fabric that absorbs the liquid from the reservoir and provides a larger surface area, and a fan. The reservoir was filled with 1.5 L aqueous solutions of glycine or sarcosine (1 M) and KOH (1 M) and the fan was run on slow setting, corresponding to an air flow rate of 3.8±0.2 m/s. The capture experiments were run at ambient temperature (21±1° C.). However, because of the water evaporation, the solution temperature was lower, averaging 16±1° C. The reservoir was replenished periodically with $H_2O$ to compensate for the evaporated water (on average the evaporation rate was 100 mL/h) and keep the amino acid concentration as constant as possible. The change in the pH of the amino acid solution was monitored in situ with a glass electrode. The amount of $CO_2$ absorbed was monitored by withdrawing 300 μL samples and analyzing their carbonate and carbamate content by ion chromatography (IC) and $^1H$ NMR spectroscopy, respectively. For NMR analyses, 900 μL of $D_2O$ was added to 100 μL of the samples, whereas for the IC analyses, the samples were diluted 10-300 fold to bring the carbonate concentration in the 30-300 ppm range.

Thermodynamic Analysis

Once the basic design elements were established, the next important step was to determine the thermodynamics of the $CO_2$ absorption and desorption, as well as of sorbent regeneration, which define the energy and efficiency boundaries for the DAC system. The energetics of the $CO_2$ absorption (equation 7) can be obtained by adding up the energetics of the elementary reactions represented by equations 1-6. The enthalpies of $CO_2$ hydration (equation 3) and of reaction with HO— to generate bicarbonate (equation 4) are already known. The heat of bicarbonate deprotonation by HO— to make $CO_3^{2-}$ (equation 5) can also be calculated from published thermodynamic data on carbonate protonation and water ionization. The remaining enthalpies for the reactions involving PyBIG and $PyBIGH_2(CO_3)(H_2O)_4$ were determined as part of this study. The enthalpies of PyBIG dissolution (equation 1) and $PyBIGH_2(CO_3)(H_2O)_4$ crystallization (equation 6) were obtained by variable-temperature solubility measurements of the two solids and van't Hoff analyses). Finally, the enthalpies of PyBIG protonation (equation 2) were obtained from variable-temperature pKa measurements by potentiometric titrations and van't Hoff analyses. The corresponding ΔH values for reactions 1-6 are listed in Table 1 below. Adding up these values results in an overall enthalpy of $CO_2$ absorption by PyBIG of −70.7 kJ/mol.

TABLE 1

Reaction enthalpies for the corresponding elementary steps involved in DAC with PyBIG.

| Equation | Reaction | ΔH (kJ/mol) | Reference |
| --- | --- | --- | --- |
| 1 | PyBIG dissolution | 42.5 | This study |
| 2 | PyBIG protonation | 43.6[a] | This study |
| 3 | $CO_2$ dissolution | −19.4 | 29 |
| 4 | $HCO_3^-$ formation | −50 | 30 |
| 5 | $CO_3^{2-}$ formation | −40.4 | 31, 32 |
| 6 | $PyBIGH_2(CO_3)(H_2O)_4$ cryst. | −47 | This study |

[a]The enthalpy for reaction 2 is composed of the sum of the first (−31 kJ/mol) and second (−37 kJ/mol) protonation enthalpies of PyBIG plus twice the enthalpy of deprotonation of water (55.8 kJ/mol).

In the above table, reference 29 corresponds to J. J. Carroll et al., *J. Phys. Chem. Ref Data* 20, 1201-1209 (1991); reference 30 corresponds to X. Wang et al., *J. Phys. Chem. A* 114, 1734-1740 (2010); reference 31 corresponds to N. McCann et al., *J. Chem. Thermodynamics* 43, 664-669 (2011); and reference 32 corresponds to J. D. Hale et al., *J. Phys. Chem.* 67, 2605-2608 (1963).

It is instructive to compare the thermodynamics of the $CO_2$ absorption by PyBIG with those of other sorbents used in DAC. For example, amine sorbents have absorption enthalpies in the range of 60-80 kJ/mol. Unlike primary or secondary amines, PyBIG does not bind directly to $CO_2$. Instead, it deprotonates water to generate hydroxide ions (equation 2), which then react with $CO_2$ to generate bicarbonate ions (equation 4). Thus, the actual $CO_2$ 'binding' by PyBIG, corresponding to equations 3-5 combined, has an enthalpy of −109.8 kJ/mol. This is essentially the same as the enthalpy of $CO_2$ absorption by aqueous NaOH. The crystallization step (equation 6) then adds −47 kJ/mol, to make the overall absorption process a combined −156 kJ/mol, which is about twice as exothermic compared to the $CO_2$ absorption by a typical amine sorbent. However, dissolution of PyBIG (equation 1), which is endothermic (+42.5 kJ/mol) and essentially offsets the exothermic crystallization in step 6, and proton transfer from water to the guanidine groups (equation 2), which is also endothermic (+43.6), brings the overall enthalpy for $CO_2$ capture by PyBIG (equation 7) to −70.7 kJ/mol.

Although the $CO_2$ desorption could theoretically be achieved by running reactions 1-6 in reverse order according to the principle of microscopic reversibility, in reality it would not be feasible as reaction 4 is practically irreversible. Such an approach would also defeat the purpose of avoiding heating the aqueous sorbent. Instead, once the loading is complete, the crystalline $PyBIGH_2(CO_3)(H_2O)_4$ is removed from solution and heated in the solid state to release the $CO_2$ gas and the water vapors. Given the completely different conditions involved, such a solid-gas-solid process must have different energetics compared to the gas-liquid-solid process involved in $CO_2$ absorption.

In order to determine the enthalpy of $CO_2$ release from $PyBIGH_2(CO_3)(H_2O)_4$, differential scanning calorimetry (DSC) was employed. DSC is a common technique used in thermal analysis of solids. The obtained DSC curve showed a series of endothermic events between 80 and 140° C., corresponding to the release of water and $CO_2$ as previously found by thermogravimetric analysis (Seipp et al., *Angew. Chem. Int. Ed.* 56, 1042-1045, 2017). Unfortunately, the extensive overlap between the peaks prevented a determination of the heats associated with each thermal event. Instead, all the peaks were integrated together to obtain the overall enthalpy of desorption for $PyBIGH_2(CO_3)(H_2O)_4$, which amounts to 223±4 kJ/mol. While the overall reaction is highly endothermic, it should be taken into account that, for each $CO_2$ molecule released from $PyBIGH_2(CO_3)(H_2O)_4$, there are four molecules of hydration that are desorbed (plus a fifth water molecule that is a bi-product of the carbonate decomposition).

In order to determine the fraction of the reaction enthalpy corresponding to the $CO_2$ release from the carbonate, anhydrous $PyBIGH_2(CO_3)$ was prepared by overnight vacuum pumping of $PyBIGH_2(CO_3)(H_2O)_4$ at 30° C. The enthalpy of the $CO_2$ release from the anhydrous carbonate salt, as measured by DSC, was found to be 75±6 kJ/mol. The difference between the measured endotherms of $PyBIGH_2(CO_3)(H_2O)_4$ and $PyBIGH_2(CO_3)$, of 148 kJ/mol, can be assigned to dehydration of the carbonate salt. This corresponds to an average of 37 kJ/mol per water of hydration, which is close to the enthalpy of vaporization for liquid water, of 40.65 kJ/mol. While a large fraction of the heat required to release the $CO_2$ is spent on water evaporation, part of the waste heat could be recovered by process modifications that involve water condensation steps in which the resulting heat is collected and re-used via heat exchangers. Alternatively, vacuum-drying operations that typically require less energy than heat drying can be employed for dehydration of $PyBIGH_2(CO_3)(H_2O)_4$ prior to $CO_2$ release. The use of renewable sources of energy, such as concentrated solar power, is also herein being considered to make the overall DAC process energy sustainable.

In addition to the enthalpies of CO2 absorption and release, another important thermodynamic parameter is the equilibrium constant for the amino acid regeneration reaction (equation 10), which defines the efficiency limit for sorbent regeneration. In the regeneration reaction, the solid PyBIG has to dissolve into the sorbent solution, deprotonate the amino acid and the bicarbonate ion, and crystallize as $PyBIGH_2(CO_3)(H_2O)_4$. In the case of the glycine sorbent, the equilibrium constant for the regeneration reaction (log $K_{reg}$) is defined by equation 11 as follows:

$$\log K_{reg} = \log K_{sp}(PyBIG) - \log K_{sp}(PyBIGH_2(CO_3)(H_2O)_4) - pK_a(Gly) - pK_a(HCO_3^-) + pK_{a1}(PyBIG) + pK_{a2}(PyBIG) \quad (11)$$

Thus, the amino acid regeneration is driven by the difference in solubility between PyBIG and $PyBIGH_2(CO_3)(H_2O)_4$, as well as the difference in basicity between glycine and bicarbonate on the one hand, and PyBIG on the other hand. The pKa values at 25° C. for the two guanidinium groups of PyBIG, as determined by potentiometric titration, are 7.6 and 8.7. On the other hand, the pKa values of glycine and bicarbonate are 9.5 and 10.3, respectively (Yang N. et al., *Ind. Eng. Chem. Res.* 53, 12848-12855, 2014). Thus, PyBIG is not sufficiently basic to drive the regeneration equilibrium to the right, and therefore, the main driving force has to come from the solubility difference between PyBIG and $PyBIGH_2(CO_3)(H_2O)_4$. A preliminary estimated value of $1.0 \times 10^{-8}$ is given for the solubility product of $PyBIGH_2(CO_3)(H_2O)_4$. As part of this study, determination of a more accurate value became possible as the exact speciation of PyBIG in solution could now be obtained based on the measured pKa values of PyBIG, resulting in a revised $K_{sp}$ for $PyBIGH_2(CO_3)(H_2O)_4$ of $1.0 \pm 0.3 \times 10^{-9}$ at 25° C. This corresponds to a very insoluble carbonate salt, on par with the natural calcite mineral ($K_{sp} = 3.3 \times 10^{-9}$). By comparison, the measured $K_{sp}$ of PyBIG at the same temperature is $1.0 \pm 0.3 \times 10^{-2}$. Thus, under ideal conditions, log $K_{reg} = 3.5$, which predicts a very efficient amino acid regeneration with PyBIG. However, under realistic conditions involving high ionic strength solutions that can significantly impact the solubilities of the various species involved through ion pairing, salting out, etc., the observed regeneration efficiency may actually be less than ideal.

Carbon Dioxide Absorption with Aqueous Glycine and Sarcosine

Figure 3A:
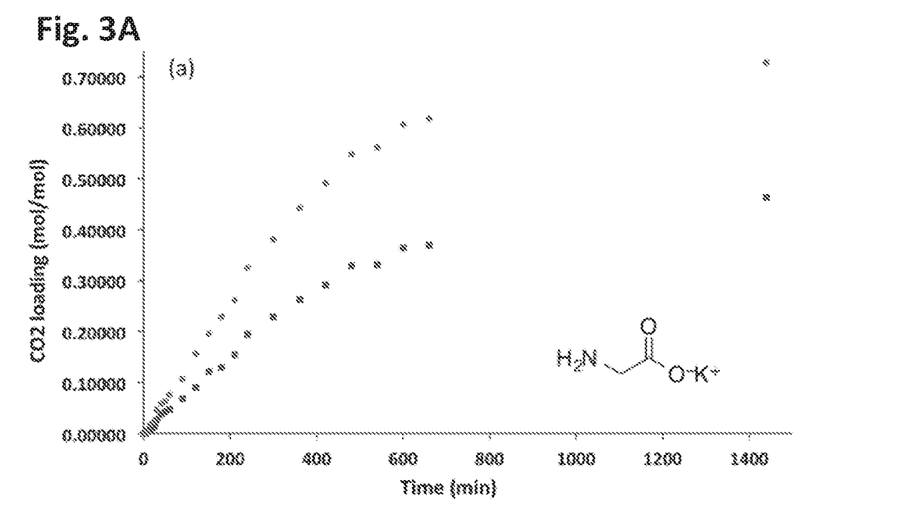
FIGS. 3A, 3B. Chart showing absorption of atmospheric $CO_2$ into a 1 M aqueous solution of glycine/KOH (FIG. 3A) or sarcosine/KOH (FIG. 3B) as a function of time. Squares and dots correspond to carbonate and total $CO_2$ (carbonate+ carbamate) loadings, respectively.
Figure 3B:
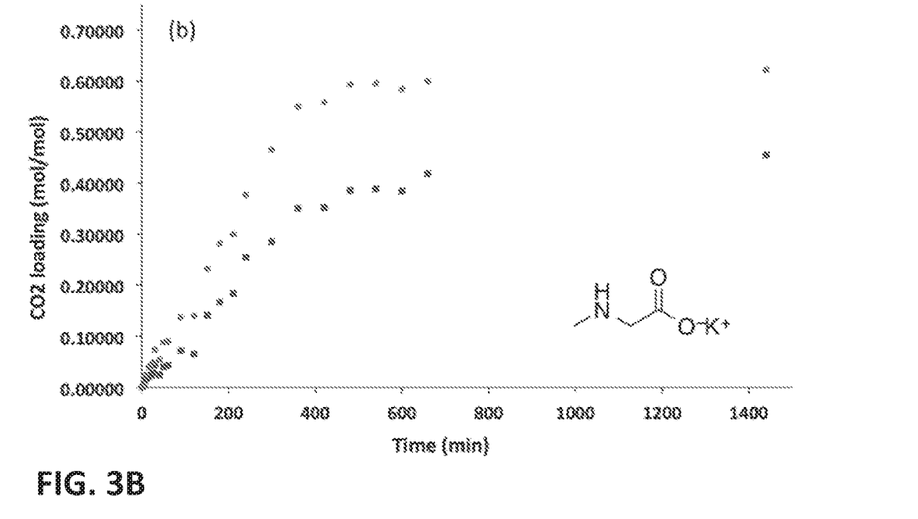

The direct air capture of $CO_2$ in this study was done with an air humidifier using aqueous amino acid sorbents (as potassium salts). The loading of $CO_2$ into 1 M aqueous solutions of potassium glycinate and sarcosinate as a function of time is shown in FIGS. 3A and 3B, respectively. The extent of $CO_2$ absorption was monitored in situ by pH measurements, and ex situ by ion chromatography (IC) and $^1$HNMR to determine the amounts of carbonate and carbamate formed. The sorption experiments were run for 24 hours and the results are summarized in Table 2 below.

Three different sorption experiments were done for each amino acid, and the reported concentrations are the average values for the three runs after 24 hours. The $CO_2$ absorption rates for sarcosine and glycine are quite similar for the first 7-8 hours, after which time the absorption rate for sarcosine levels off abruptly, whereas the corresponding absorption rate for glycine slows down more gradually. While the reaction rates of $CO_2$ with both sarcosine and glycine are believed to be high (e.g., ca. 18.6 and 13.9 kM/s, respectively, at 25° C.) the relatively long times required to reach $CO_2$ saturation with both sarcosine and glycine sorbents is primarily due to the very low concentration of $CO_2$ in air. The design of the air humidifier used in this study, which offers a small (<1 m$^2$) air-water interfacial area relative to the volume of the sorbent (1.5 L), also limits the rate of $CO_2$ upload. After 24 hours, the average $CO_2$ loading for glycine (0.77±0.04 mol/mol) was slightly higher than for sarcosine (0.69±0.05 mol/mol). The difference can be accounted for by the larger amount of carbamate formed with glycine (0.22±0.06 M) compared to sarcosine (0.15±0.02 M).

Sorbent Regeneration by Carbonate Crystallization with PyBIG

The $CO_2$-loaded sorbents were stirred with a suspension of PyBIG (0.5 molar equivalents relative to $CO_2$) at room temperature (~25° C.), which resulted in crystallization of $PyBIGH_2(CO_3)(H_2O)_4$ and regeneration of the anionic forms of the amino acids, according to equation 10. The formation of crystalline $PyBIGH_2(CO_3)(H_2O)_4$ was confirmed by powder X-ray diffraction (PXRD), which revealed after 24 hours a mixture of PyBIG.2.5H$_2$O and the carbonate salt.

The amino acid solutions (5 mL) were placed in 20 mL vials and PyBIG.2.5H$_2$O was added as a solid. The amount of PyBIG added varied with the $CO_2$ loading of the solution; the optimum amount was found to be 0.5 molar equivalents relative to the $CO_2$ absorbed (moles $CO_2$/moles PyBIG=2). The resulting suspensions were shaken at 1000 rpm on a vortex mixer, adding a teflon-coated micro stir bar to each vial to aid in the mixing. Subsamples (50 μL) were withdrawn hourly for the first 8 hours and then after 24 hours, using a 0.22 μm syringe filter to remove solid particulates from solution prior to preparing samples for $^1$H NMR and IC. The subsamples were first diluted with 450 μL of D$_2$O, then left at room temperature for 24 hours before they were analyzed by NMR spectroscopy. For IC analyses, 20 μL of the solutions used for NMR analyses were diluted with 980 μL of deionized H$_2$O. At the end of the regenerations, the final solids were filtered and analyzed by PXRD for phase identification.

Figure 4A:
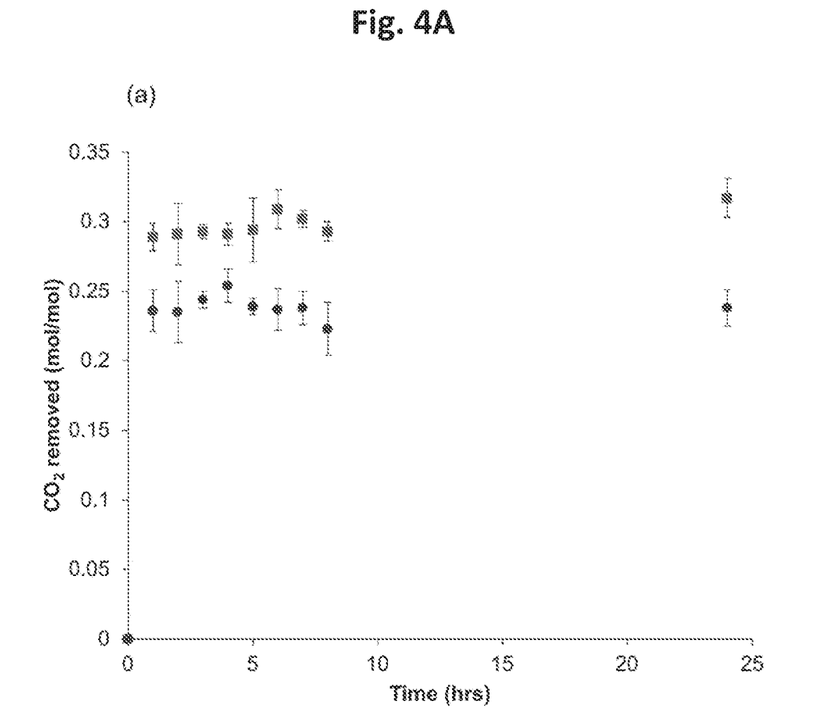
FIG. 4A: Chart showing regeneration of glycine (dots) and sarcosine (squares) sorbents with PyBIG, wherein the total amount of $CO_2$ removed (mol/mol) is shown as a function of time.

The concentrations of carbonate and carbamate in the amino acid solutions were monitored by IC and NMR, respectively, and the total amount of $CO_2$ removed as a function of time is plotted in FIG. 4A. More than 90% of the total amount of $CO_2$ removed was released from the sorbent within the first hour, and longer regeneration times only led to marginal improvements. The results after 24 hours regeneration time are summarized in Table 3 below.

TABLE 2

Carbon dioxide loading values for DAC with 1M aqueous solutions of potassium glycinate and sarcosinate

| Sorbent | pH (initial/final) | Carbonate[a] (M) | Carbamate (M) | Total CO$_2$ (M) |
|---|---|---|---|---|
| Glycine (1M) | 12.31/9.52 | 0.54 ± 0.08 | 0.22 ± 0.06 | 0.77 ± 0.04 |
| Sarcosine (1M) | 12.92/9.99 | 0.54 ± 0.07 | 0.15 ± 0.02 | 0.69 ± 0.05 |

[a] As the sum of $CO_3^{2-}$ and $HCO_3^-$ concentrations.

TABLE 3

Regeneration results for the 1M aqueous solutions of potassium glycinate and sarcosinate after stirring with a suspension of PyBIG (0.5 molar equiv) for 24 hours.

| Sorbent | pH (initial/final) | Carbonate (M) | Carbamate (M) | Total CO$_2$ (M) |
|---|---|---|---|---|
| Glycine (1M) | 9.63/10.33 | 0.33 | 0.05 | 0.38 |
| Sarcosine (1M) | 9.99/10.53 | 0.29 | 0.03 | 0.32 |

Most of the $CO_2$ from each sorbent is released within an hour, and longer regeneration times only led to marginal improvements. The cyclic capacity, defined as the difference between the maximum $CO_2$ loading observed after absorption and the minimum $CO_2$ loading measured after regeneration, is 0.35 and 0.31 mol/mol for the glycine and sarcosine sorbents, respectively.

Figure 4B:
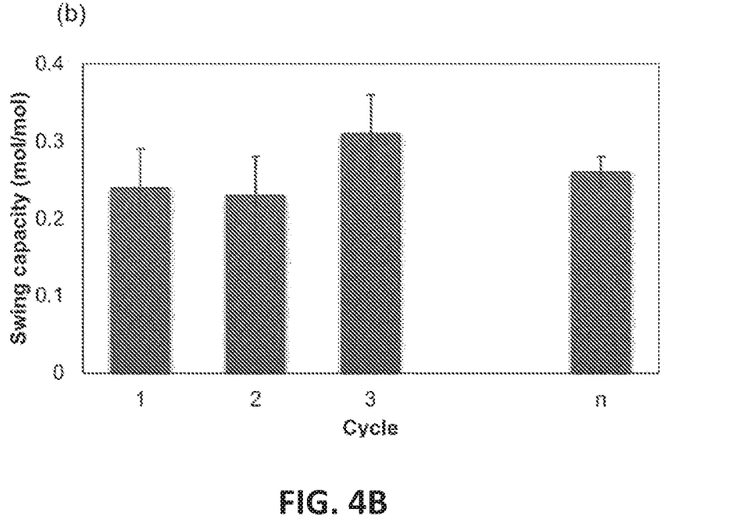
FIG. 4B: Graph showing measured swing capacity for three consecutive loading/ regeneration cycles with sarcosine/PyBIG. The column on the right (cycle n) corresponds to the measured swing capacity using PyBIG that was 'aged' at 120° C. in open air for a week.

The average swing capacity, defined as the difference between the maximum $CO_2$ loading observed after 24 hours of absorption and the minimum $CO_2$ loading measured after 24 hours of regeneration (based on three separate runs), was 0.28±0.06 and 0.31±0.05 mol/mol for the glycine and sarcosine sorbents, respectively. FIG. 4B shows the measured swing capacity for three consecutive loading/regeneration cycles with sarcosine/PyBIG. As shown in FIG. 4B, the swing capacity remained relatively constant over three consecutive loading/regeneration cycles. However, many more cycles will have to be run to test the long-term robustness of this DAC system. Although the room-temperature crystallization-based sorbent regeneration employed herein circumvents the heating of the amino acid sorbent, thereby extending its operational lifetime, the long-term stability of PyBIG that must be thermally regenerated remains a concern, as its degradation over time would lead to a gradual decrease in the cyclic capacity. In order to test the thermal stability of PyBIG, the compound was subjected to accelerated aging by heating it at 120° C. in open air for a week, which is the equivalent of 336 thermal regeneration cycles (based on a typical 30 minute regeneration time). The thermogravimetric analysis showed minimal weight changes over this extended period of heating, with only 0.5% weight loss after the initial 35.3% corresponding to the $CO_2$ and $H_2O$ loss. The 'aged' PyBIG was subsequently used in a sarcosine regeneration cycle and the measured swing capacity of 0.26±0.02 mol/mol was very similar to the corresponding values measured with fresh PyBIG (FIG. 4B), attesting to the thermal stability of the guanidine compound.

Regeneration of the amino acid sorbents can also be achieved in a traditional fashion, by boiling the aqueous solutions under reflux. After one hour of refluxing, the total $CO_2$ removed from the glycine and sarcosine sorbents was 0.31 and 0.30 mol/mol, respectively, which are comparable with the corresponding values observed in the regenerations using PyBIG. With longer reaction times, the boiling regenerations outperforms the regenerations with PyBIG, with the total $CO_2$ swing capacity increasing to 0.47 and 0.45 mol/mol after 4 hours of refluxing the glycine and sarcosine solutions, respectively. However, such long refluxing times are expected to come at a cost in terms of energy consumption and sorbent degradation.

Carbon Dioxide Release and Regeneration of the PyBIG Compound with Concentrated Solar Power The $CO_2$ release from the $PyBIGH_2(CO_3)(H_2O)_4$ crystals was conducted by solar heating with a solar oven. The oven consists of a vacuum-insulated borosilicate tube placed in the focal point of two adjustable parabolic reflectors. The temperature inside the tube was monitored with a thermocouple. The $PyBIGH_2(CO_3)(H_2O)_4$ samples 36.4-45.0 mg, 0.095-0.118 mmol) were loaded in 1 mL glass vials, which were placed inside the oven tube. The solar oven was then placed in the full sun and oriented to capture the maximum amount of sunlight. The temperature was ramped to the targeted values of 120° C., 130° C., 140° C., 150° C., or 160° C. as fast as possible (typically within 3 to 10 minutes), then held within ±2° C. by intermittently moving the oven out of the sun, or/and closing the reflectors. The samples were subsequently removed from the tube, allowed to cool to room temperature, and weighed to determine their mass loss. The resulting yellow solids were analyzed by FTIR to confirm the disappearance of the carbonate and water peaks. The solar regeneration experiments were repeated three times at each temperature, and the average values and standard deviations calculated.

This preliminary study indicated that the $PyBIGH_2(CO_3)(H_2O)_4$ crystals release the $CO_2$ and water vapor upon mild heating at temperatures of 80-120° C., and regenerate the PyBIG compound quantitatively. However, considering that this transformation is highly endothermic, the possibility of using concentrated solar power to render the process more energy sustainable was explored. For the initial small-scale proof of concept, a solar oven was used to heat solid $PyBIGH_2(CO_3)(H_2O)_4$ samples (~38 mg, 0.1 mmol) at five different temperatures ranging between 120 and 160° C. The extent of the reactions was monitored by the samples' weight loss, as shown in Table 4 below. FTIR analyses corroborated the release of $CO_2$, most evidently noticeable by the disappearance of the strong peak at 1361 $cm^{-1}$ corresponding to the stretching mode of the carbonate anion. For comparison, no $CO_2$ release was observed from $CaCO_3$ after two hours of solar heating at 160° C., which is not surprising considering that metal carbonates typically require temperatures of at least 800° C. to regenerate the alkaline sorbent. Thus, these results demonstrate that concentrated solar power can effectively release the $CO_2$ from the carbonate crystals and regenerate the PyBIG compound quantitatively.

TABLE 4

Carbon dioxide release from $PyBIGH_2(CO_3)(H_2O)_4$ and regeneration of PyBIG by heating with concentrated solar power. Three different measurements were done at each temperature, and the reported % weight losses and regeneration yields are the average values.

| T (° C.) | Heating time (min) | Weight loss (%) | Regeneration yield (%) |
|---|---|---|---|
| 120 | 30 | 32.3 ± 0.8 | 92 ± 2 |
| 130 | 15 | 32.3 ± 0.8 | 92 ± 2 |
| 140 | 10 | 33.2 ± 0.8 | 95 ± 2 |
| 150 | 5 | 32.5 ± 0.8 | 93 ± 2 |
| 160 | 2 | 33.8 ± 0.3 | 96 ± 1 |

These results demonstrate that concentrated solar power can be effectively used for quick release of the $CO_2$ from the carbonate crystals and regeneration of the PyBIG compound in near quantitative (92-96%) yield. The regeneration of PyBIG requires relatively low temperatures that are easily attainable with simple parabolic-trough solar concentrators, in direct contrast to traditional alkaline sorbents that would require more elaborate solar reactor designs to achieve the much higher temperatures needed for regeneration. Furthermore, solid-state regeneration of PyBIG is fast in comparison to aqueous sorbents, for which a substantial amount of energy needs to be expanded for heating and evaporating water. For example, under the same conditions (30 minutes, 120° C.), the regeneration yield of an aqueous $K_2CO_3$ sorbent was only 15%, compared to the 92% regeneration yield for PyBIG.

CONCLUSIONS

This study demonstrated a small-scale DAC system using simple, off-the-shelf equipment and readily available chemicals. Effective $CO_2$ absorption with aqueous glycine and sarcosine sorbents using a household humidifier was followed by room temperature crystallization of a guanidinium carbonate salt of very low aqueous solubility, and $CO_2$ desorption from the carbonate crystals using concentrated solar power. This approach combines the benefits of an aqueous sorbent, such as fast $CO_2$ absorption rates, easy handling, and low maintenance, with the advantages of solid-state $CO_2$ desorption that avoids much of the energy penalty associated with heating and evaporating aqueous solutions, and minimizes sorbent degradation. Furthermore, the amino acid sorbents offer an environmentally friendly alternative to the more traditional sorbents, such as amines or NaOH.

One important issue that requires serious consideration is how to scale up the guanidinium carbonate crystallization and handle large volumes of solid. Along this line, much can be learned from the design of the post-combustion $CO_2$ capture technologies involving precipitating amino acid sorbents (DECAB Plus), or aminosilicone sorbents. In these processes, the solids are removed from solution using solid-liquid separators, such as cyclones or decanters, then transported with the help of extruders in a continuous feed mode. The effectiveness of these processes depends to a large extent on a number of crystallization parameters and characteristics of the guanidinium carbonate precipitate, such as kinetics of crystallization, particle size distribution, and crystal habit, which need to be thoroughly investigated as part of technology development and maturation.

In addition to demonstrating the initial proof-of-concept, this study also identified a number of limitations for the current DAC system and provided guidelines for the design and optimization of future DAC technologies. First, while the amino acid sorbents react fast with $CO_2$, the air humidifier used in this study is not optimized for DAC as it provides a relatively small air-water interfacial area, which limits the overall $CO_2$ uptake rate. Also, as designed, the humidifier evaporates large amounts of water, which in the case of DAC is a disadvantage. Combining the amino acid sorbents with better air-liquid contactors that optimize the air-water interfacial area and minimize the water loss may lead to more efficient DAC systems. Second, while sorbent regeneration and carbonate crystallization with PyBIG is adequate, with observed cyclic capacities of 0.3-0.35 mol/mol, the regeneration process could be significantly improved by replacing the PyBIG compound with a more soluble and more alkaline (higher pKa for the guanidine groups) analogue that would push the equilibrium for the regeneration reaction further to the right, according to equation 11. The kinetics of crystallization and sorbent regeneration are also critical in achieving an efficient closed cycle process that continuously circulates the sorbent between the sorption and regeneration units. Finally, although the $CO_2$ desorption from crystalline $PyBIGH_2(CO_3)(H_2O)_4$ avoids much of the energy penalty associated with heating and evaporating aqueous solutions, the enthalpy of desorption of the carbonate crystals is strongly endothermic, mainly due to the inclusion of water in the crystals. Engineering carbonate crystals that are anhydrous, or can release the $CO_2$ at lower temperatures to avoid water vaporization, may improve the energy efficiency of the DAC process. On the other hand, employing renewable energy sources, such as concentrated solar power, as demonstrated in this study, or low-grade waste heat, may alleviate much of this issue.

While there have been shown and described what are at present considered the preferred embodiments of the invention, those skilled in the art may make various changes and modifications which remain within the scope of the invention defined by the appended claims.

What is claimed is:

1. A method for removing carbon dioxide from a gaseous source, the method comprising:
   (i) contacting said gaseous source with an aqueous solution of a carbon dioxide sorbent that reacts with carbon dioxide to form an aqueous-soluble carbonate or bicarbonate salt of said carbon dioxide sorbent;
   (ii) contacting the aqueous solution from step (i) with a carbon dioxide complexing compound, which is different from the carbon dioxide sorbent, after the aqueous-soluble carbonate or bicarbonate salt of said carbon dioxide sorbent is formed in step (i), to result in precipitation of a carbonate or bicarbonate salt of said carbon dioxide complexing compound and regeneration of the carbon dioxide sorbent; and
   (iii) removing the precipitated carbonate or bicarbonate salt from the aqueous solution in step (ii) to result in a solid form of said carbonate or bicarbonate salt of the carbon dioxide complexing compound;
   wherein said carbon dioxide complexing compound has the following structure:

and wherein said carbonate or bicarbonate salt of said carbon dioxide complexing compound has the following structure:

wherein:
A is a ring-containing moiety or a bond;
one or more of the hydrogen atoms in Formulas (1), (1a), and (1a') may be replaced with one or more methyl groups;
$X^{m-}$ is a carbonate or bicarbonate anion, with m being 1 for bicarbonate and 2 for carbonate; and
n is 0.5, 1, or 2;
provided that n×m=2 in the case of Formula (1a), and n×m=1 in the case of Formula (1a').

2. The method of claim 1, wherein said carbon dioxide sorbent is selected from organoamines, alkali hydroxides, alkali carbonates, and alkaline earth hydroxides.

3. The method of claim 1, wherein said carbon dioxide sorbent is an organoamine.

4. The method of claim 3, wherein said organoamine is an amino acid.

5. The method of claim 4, wherein said amino acid is selected from glycine and N-alkylglycines, wherein alkyl is independently selected from hydrocarbon groups containing 1-6 carbon atoms.

6. The method of claim 1, further comprising: (iv) regenerating the carbon dioxide complexing compound by subjecting the carbonate or bicarbonate salt of said carbon dioxide complexing compound to heat, vacuum, or both, sufficient to result in release of carbon dioxide gas emanating from said carbonate or bicarbonate salt of said carbon dioxide complexing compound along with simultaneous restoration of the carbon dioxide complexing compound, wherein the released carbon dioxide gas is either quarantined for storage and/or converted into a chemical substance or feedstock.

7. The method of claim 6, wherein said carbonate or bicarbonate salt of said carbon dioxide complexing compound is heated to a temperature within a range of 30° C.-250° C.

8. The method of claim 6, wherein said carbonate or bicarbonate salt of said carbon dioxide complexing compound is heated to a temperature within a range of 40° C.-160° C.

9. The method of claim 6, wherein said heat is provided by a renewable energy source.

10. The method of claim 9, wherein said renewable energy source is solar energy.

11. The method of claim 10, wherein said solar energy is a direct solar heat concentrator.

12. The method of claim 1, wherein said gaseous source is contacted intimately with said aqueous solution of a carbon dioxide sorbent by use of an air-liquid contact facilitator, wherein said air-liquid contact facilitator increases surface area of said aqueous solution to increase the air-liquid contact area between the gaseous source and said aqueous solution.

13. The method of claim 12, wherein said air-liquid contact facilitator is a humidifying device that contains a reservoir of the aqueous solution containing the carbon dioxide sorbent, and wherein said humidifying device increases the surface area of said aqueous solution by wicking said aqueous solution or forming a mist of said aqueous solution.

14. The method of claim 1, wherein A is a monocyclic ring.

15. The method of claim 14, wherein said monocyclic ring is a five-membered, six-membered, or seven-membered ring.

16. The method of claim 1, wherein A is a carbocyclic ring or ring system.

17. The method of claim 16, wherein said carbocyclic ring or ring system is unsaturated.

18. The method of claim 17, wherein A comprises a benzene ring.

19. The method of claim 1, wherein A is a heterocyclic ring or ring system.

20. The method of claim 19, wherein said heterocyclic ring or ring system is unsaturated.

21. The method of claim 19, wherein said heterocyclic ring or ring system contains at least one nitrogen ring atom.

22. The method of claim 19, wherein A comprises a pyridine ring.

23. The method of claim 1, wherein A is a bond.

* * * * *